United States Patent [19]

Lieb et al.

[11] 4,015,489

[45] Apr. 5, 1977

[54] DENTAL HANDPIECE AND WRENCH THEREFOR

[75] Inventors: Nathaniel H. Lieb, Narberth; Franklin W. Kerfoot, Jr., Newtown Square; Richard A. Wallace, Audubon, all of Pa.

[73] Assignee: Star Dental Manufacturing Co., Inc., West Conshohocken, Pa.

[22] Filed: July 25, 1975

[21] Appl. No.: 599,265

Related U.S. Application Data

[62] Division of Ser. No. 476,749, June 5, 1974, Pat. No. 3,947,966, which is a division of Ser. No. 217,745, Jan. 14, 1972.

[52] U.S. Cl. .................................................. 81/55
[51] Int. Cl.² ........................................ B25B 27/00
[58] Field of Search .................... 81/71, 55; 32/27

[56] References Cited

UNITED STATES PATENTS

| | | | |
|---|---|---|---|
| 2,752,809 | 7/1956 | Lehmann | 81/55 |
| 3,120,706 | 2/1964 | Turchi et al. | 32/27 |
| 3,325,899 | 6/1967 | Staunt | 32/27 |
| 3,394,623 | 7/1968 | Kinakin | 81/55 |

*Primary Examiner*—James L. Jones, Jr.
*Attorney, Agent, or Firm*—Caesar, Rivise, Bernstein & Cohen

[57] ABSTRACT

A dental handpiece and a wrench adapted to be used in combination with the handpiece for securing a dental bur in the handpiece. The handpiece includes a turbine housing, a rotor shaft and a collet threadedly secured in the rotor shaft. The wrench has a plurality of fingers which are adapted to be received in the rotor shaft, and a shaft rotatably mounted in a tube from which the fingers project. The wrench shaft is adapted to threadedly advance or retract the collet relative to the rotor shaft.

5 Claims, 13 Drawing Figures

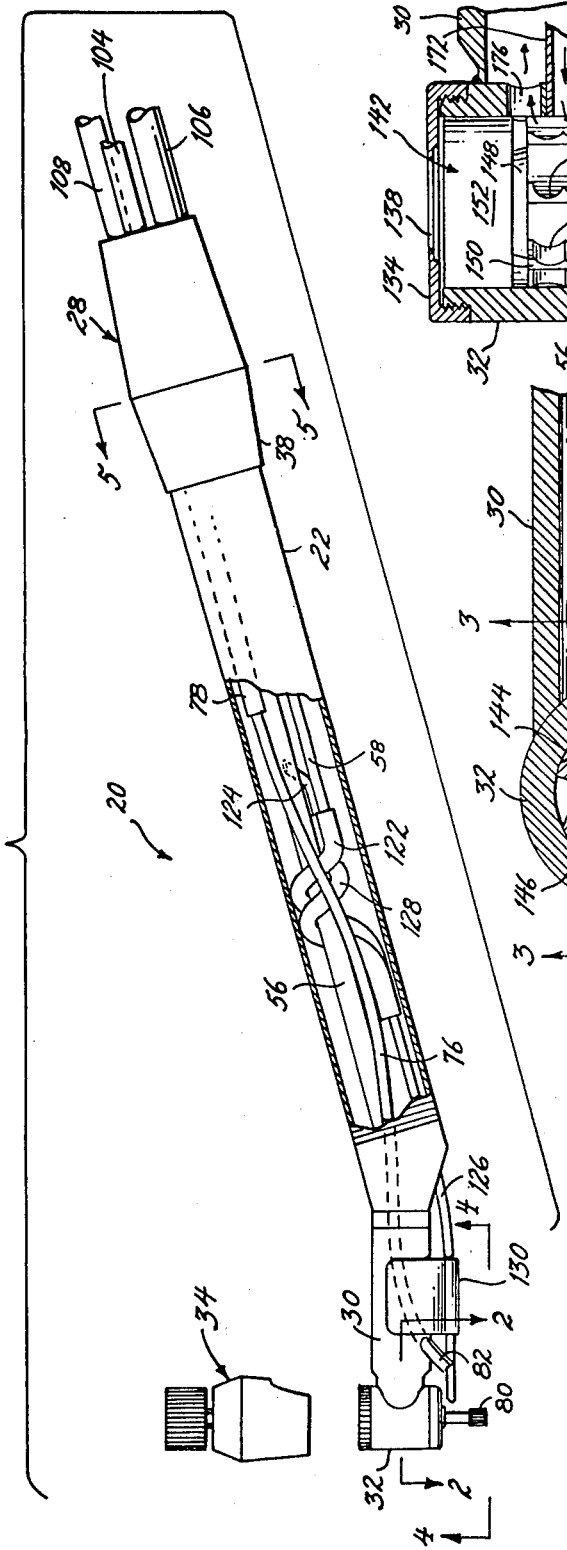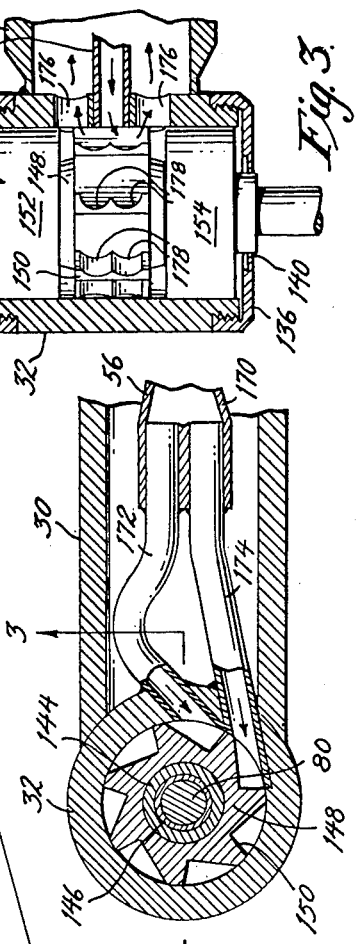

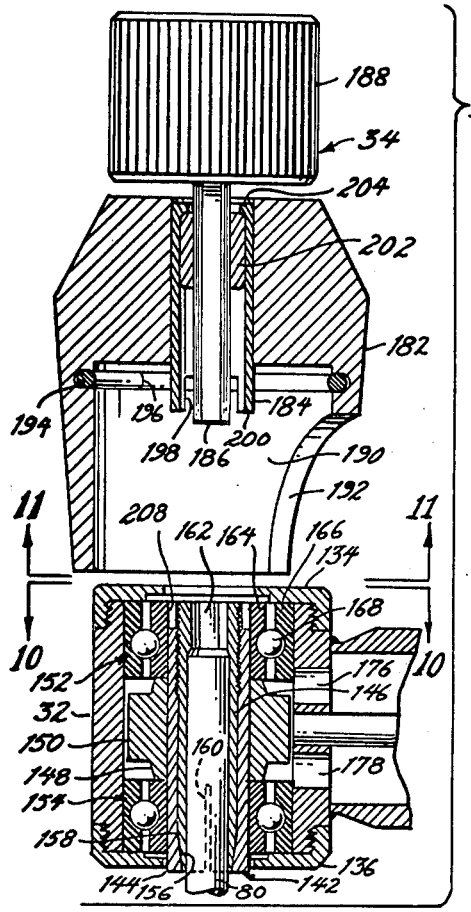
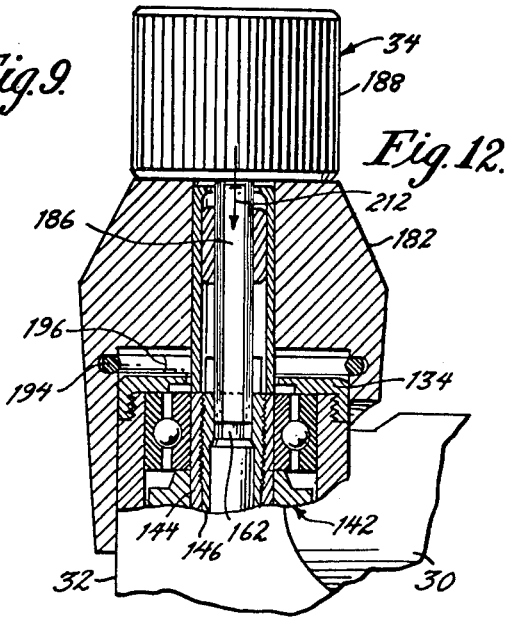
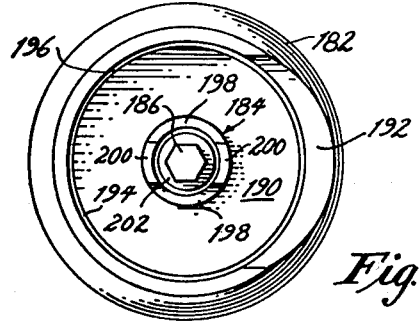
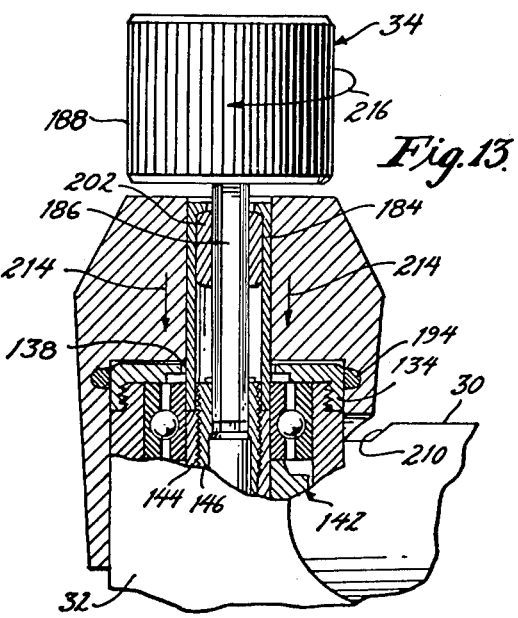
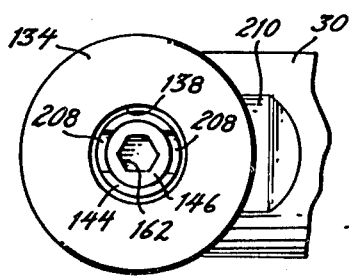

DENTAL HANDPIECE AND WRENCH THEREFOR

This application is a division of United States application Ser. No. 476,749, filed June 5, 1974, now U.S. Pat. No. 3,947,966, which is in turn a division of United States application Ser. No. 217,745 filed Jan. 14, 1972 and entitled Air Driven Dental Handpiece.

This invention relates to a dental handpiece, and more particularly, to a novel air driven dental handpiece that includes a novel turbine, a novel internal light system and a novel wrench for securing a dental bur in the handpiece.

It is now common practice in the dental art to supply rotative power to a dental handpiece through the use of an air driven rotor or turbine. Extremely high speeds have been attained utilizing pneumatically driven dental handpieces. However, one of the problems that has risin with the air driven dental handpieces is that the turbine housing of the handpiece has been found to be too large to enable the dentist to have complete facility of use of the handpiece when working on the posterior teeth. The size of the turbine housing has been limited, however, by the necessity for supplying sufficient power to the rotating bur in order to permit it to accomplish its intended work. Thus, it is a necessity to sacrifice the size in order to obtain sufficient power for the rotating bur.

In one aspect of the device of this invention, the diameter of the turbine has been reduced 25%, while at the same time obtaining all of the power of the larger diameter turbine. This is accomplished by utilizing a turbine having blades with arcuate recesses formed therein and by utilizing a dual or tandom jet of air directed against the turbine blades.

In another aspect of this invention, an improvement is made in connection with a wrench for rotating a collet to secure the dental bur in place. In this aspect of the invention, the wrench is an improvement on the wrenches disclosed in U.S. Pat. Nos. 3,120,706 and 3,325,899.

Originally, the collet used for securing a bur in an air driven dental handpiece comprised an elastic sleeve formed from rubber or plastic. The first improvement on the collet for an air driven dental handpiece is that disclosed in aforementioned U.S. Pat. No. 3,120,706. In this patent, a collet is threadedly secured within the rotor shaft. The collet is rotated relative to the shaft in order to insert a bur and lock it in place or in order to remove the bur.

As disclosed in this patent, the rotor is prevented from rotating by a finger that is inserted through the rotor housing into the rotor blades while a hexagonal wrench is inserted in the upper end of the collet in order to rotate the collet.

An improvement on this type of rotor securement has been provided by extending the lower end of the rotor shaft adjacent the position in which the bur is inserted. This extension has a non-circular or hexagonal cross-section. A wrench is fitted upon the extension to hold the rotor stationary as the collet is rotatably adjusted therein from the opposite end. The problem presented by this structure is that the hexagonal extension, if made large enough for secure attachment of a rotor-locking wrench, may cause serious injury to a patient should the hexagonal surfaces contact oral membranes or teeth during the high speed drilling operation. If, on the other hand, the extension is reduced in size to minimize the dangers to patients, the surfaces of the extension will be too small to provide secure attachment for a wrench without rapid wear of deformation.

A later improvement on the locking mechanism for the rotor is the use of a unitary wrench which will lock the rotor in place and provide a means for rotating the collet relative to the rotor. This wrench is disclosed in aforementioned U.S. Pat. No. 3,325,899. This wrench is advantageous in that there are no openings in the wall of the turbine housing, and no extensions on the rotor shaft are necessary. Instead, the wrench includes pins which pass through the upper end cap on the turbine housing and into openings in a flange on the rotor shaft. This locks the rotor shaft in place, and then a stem having a hexagonal cross-section, which is inserted in the upper end of the collet, is then rotated to expand or compress the jaws of the collet.

The wrench of the device of this invention includes all of the advantages of the device disclosed in U.S. Pat. No. 3,325,899, while at the same time possessing a number of additional advantages of its own. There are no locking pins on the device of this invention, and accordingly it is unnecessary to have holes for the pins in the end cap of the turbine housing. Instead, the opening in the end cap is sufficiently large to permit a sleeve to pass therethrough. The sleeve includes a pair of arcuate fingers that is received in arcuate slots in the rotor. The wrench includes a housing which is releasably secured to the turbine housing, and since the sleeve is secured to the wrench housing, the rotor will be prevented from rotating when the fingers of the sleeve are inserted in the rotor. Thereafter, a stem having a hexagonal cross-section is used to rotate the collet.

Since the wrench is not secured to the end cap, as is the case with the pins passing through holes in the end cap, there is no fear of loosening the end cap when the wrench is placed on the turbine housing. Additionally, since the slots in the rotor are visible from the exterior of the handpiece, there is no problem with attempting to insert pins through the end cap and blindly insert them in holes in an annular flange on the rotor. Additionally, since no flange is necessary on the rotor of the device of this invention, the height of the turbine housing is kept at a minimum.

In a third aspect of the device of this invention, a novel fiber optic system is provided for the handpiece. There are now fiber optic systems in use on dental handpieces which are used to focus light at the point where a rotating bur meets the tooth. The system commonly in use comprises a fiber optic bundle that is secured on the exterior of the handpiece by a clip. These units cause the handpiece to be bulky and uncomfortable to use. Additionally, the systems comprise a single light source at the terminus of the system, and this can result in blockage of the light in use.

In the handpiece of this invention, the entire system is contained within the handpiece, with the exception of two lights which project from the handpiece and focus on the rotating bur. Having the dual light sources possesses a number of advantages over the single light source of the prior devices. Thus, there is no need to adjust the lights when working in different intra-oral positions, since there will be no total blockage of the light, as there is with a single light source. Additionally, the dual light system eliminates shadows on the bur, which occur with the single light system. Another advantage of the device of this invention is that the handpiece is readily usable with or without the fiber optic system, and accordingly the fiber optic system will not interfere in any way if a head without a fiber optic system replaces the one with the fiber optic system.

It is accordingly an object of this invention to provide a novel air driven dental handpiece.

It is another object of this invention to provide a novel wrench to be used in combination with an air driven dental handpiece having a threadedly secured collet in the rotor shaft.

It is a further object of this invention to provide a dental handpiece having a novel fiber optic system therein.

It is yet a further object of this invention to provide an air driven dental handpiece having a novel air supply for the turbine.

These and other objects of this invention are accomplished by providing a dental handpiece comprising a hollow handle, a turbine housing mounted at one end of said handle, said turbine housing having an air turbine rotatably mounted therein, and means within said handle for delivering air to said turbine, said air delivering means comprising a pair of spaced tubes in fluid communication with said turbine housing, with each of said tubes being adapted to supply air to rotate said turbine at different positions on said turbine.

Other objects and many of the attendant advantages of this invention will be readily appreciated as the same becomes better understood by reference to the following detailed description when considered in connection with the accompanying drawings wherein:

FIG. 1 is an exploded side elevational view, partially broken away, of the air driven dental handpiece and wrench of this invention;

FIG. 2 is an enlarged sectional view taken along the line 2—2 of FIG. 1;

FIG. 3 is a sectional view taken along the line 3—3 of FIG. 2;

FIG. 9 is an exploded sectional view of the turbine and wrench of the handpiece of this invention;

FIG. 10 is a top plan view of the turbine housing, and taken in the direction of line 10—10 of FIG. 9;

FIG. 11 is a bottom plan view of the wrench, and taken in the direction of line 11—11 of FIG. 9;

FIG. 12 is a sectional view showing the first position of the wrench when it is mounted on the handpiece; and FIG. 13 is a sectional view similar to FIG. 12, and showing the final position of the wrench after its mounting on the handpiece.

Figure 4:
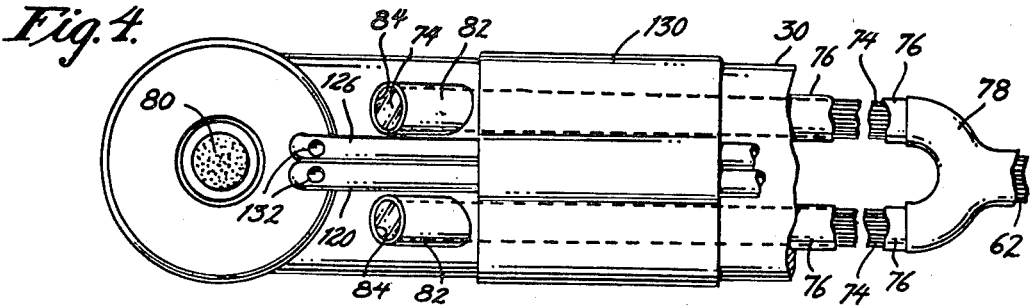
FIG. 4 is an enlarged bottom plan view of the forward portion of the air driven dental handpiece of this invention, and taken in the direction of the line 4—4 of FIG. 1.

Referring now in greater detail to the various figures of the drawings wherein like reference characters refer to like parts, an air driven dental handpiece embodying the present invention is generally shown at 20 in FIG. 1. Device 20 basically comprises a handle 22 having a connector sleeve 28 secured at the rear thereof. Handle 22 includes an angled neck 30 and a turbine housing 32 mounted perpendicularly to nech 30. A wrench used in connection with the chucking mechanism of the turbine is generally shown at 34 in FIG. 1.

Figure 6:
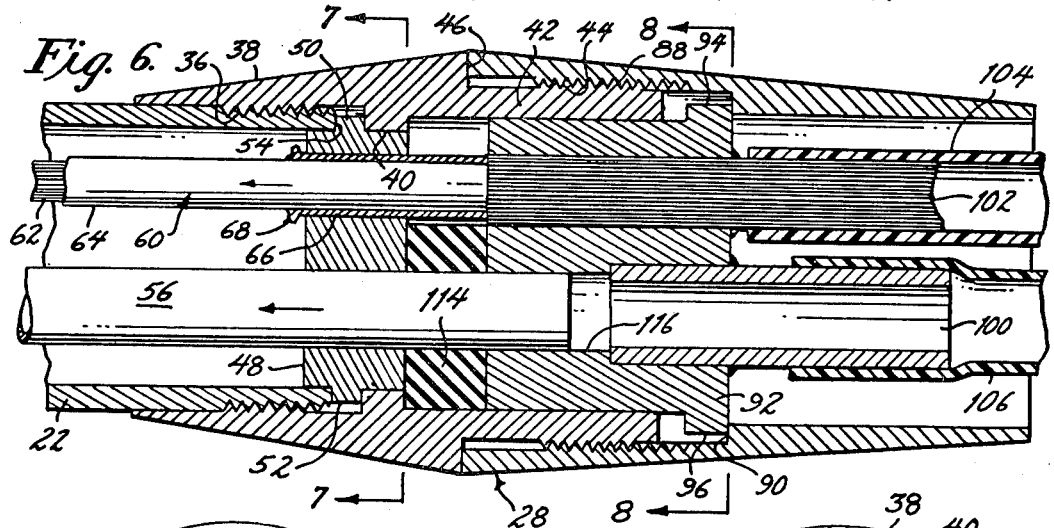
FIG. 6 is a sectional view taken along the line 6—6 of FIG. 5.

As best seen in FIG. 6, the handle 22 comprises a hollow tube, and is externally threaded at its rear end, as shown at 36. An adaptor nut 38 is threadedly secured on the rear end of handle 22. Adaptor nut 38 includes an inwardly projecting annular shoulder 40. A cylindrical portion 42 extends rearwardly on nut 38. Portion 42 is externally threaded, as shown at 44. Connector sleeve 28 is threadedly secured on cylindrical portion 42, and its forward end abuts shoulder 46 on adaptor nut 38.

A plate 48 is positioned within handle 22 at the rear end thereof. Spacer 48 includes an upper lip 50 and a lower lip 52. The spacer is held in place by securing the lips 50 and 52 between the rear edge 54 of handle 22 and shoulder 40 of adaptor nut 38.

Figure 7:
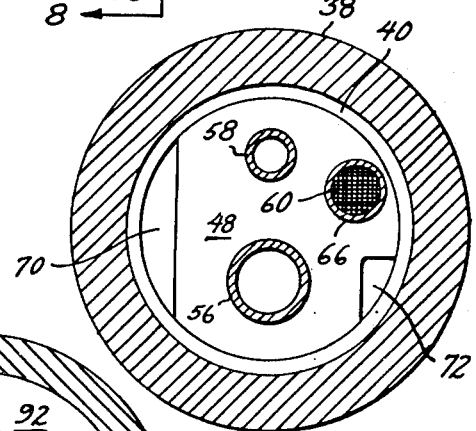
FIG. 7 is a sectional view taken along the line 7—7 of FIG. 6.

As best seen in FIG. 7, an air tube 56, a water tube 58 and a fiber optic bundle 60 pass through openings in plate 48. The fiber optic bundle comprises a plurality of individual glass fibers having a resilient plastic sleeve thereover. Preferably, the plastic sleeve comprises an elastomeric impregnation which will soak into the interstitial spaces between the individual fibers which are near the periphery of the bundle and hold the bundle together, while retaining flexibility. The elastomeric material can be any material known to the art for coating and encapsulating light transmitting glass fibers, such as a silicone rubber of polyvinyl chloride. The glass fibers are shown schematically at 62 in FIG. 6 and the elastomeric impregnant and covering sleeve is shown at 64 in FIG. 6.

A metal sleeve 66 is positioned at the rear end of the fiber optic bundle 60 and telescoped thereover. Sleeve 66 includes a rear annular lip 68. The sleeve 66 is adhesively secured to fiber optic bundle 60. Sleeve 66 is slidably mounted in plate 48, and the lip 68 prevents the bundle from being pulled rearwardly out of plate 48.

Referring to FIG. 7, it is seen that plate 48 is non-circular in cross-section. Thus, there is an opening 70 between one edge of plate 48 and the internal wall of adaptor nut 38 and a second opening 72 between the edge of plate 48 and the internal wall of adaptor nut 38. Openings 70 and 72 provide a channel for the exhausting of air that is used to drive the turbine, as will be explained hereinafter.

At an intermediate point between sleeve 66 and the forward end of handle 22, the glass fiber bundle 62 is split into two smaller bundles 74 (FIG. 4). This is easily accomplished since the large plurality of individual glass fibers can readily be divided or bifurcated into two or more equal, or unequal, branches. The two branches 74 of the glass fibers are then placed in stainless steel tubes 76.

The glass fibers 62 and branches 74 form a Y-shaped junction 78 (FIG. 4). The glass fibers can be covered at the junction by any means known to the art. The critical feature of the covering is that the glass fibers not be exposed at that point. By way of example, the fibers at the junction can be covered in the same manner as the other fibers are covered, that is, impregnating and coating the fibers with an elastomeric material. Alternatively, a Y-shaped sleeve can be provided which will be cemented to the stainless steel tubes 76 and the sleeve 64 covering the glass fibers.

As seen in FIGS. 1 and 4, the stainless steel tubes 76 containing the glass fiber bundles 74 therein extend along the handle 22, and project from the handle adjacent a dental bur 80 which is secured in the chucking mechanism of the turbine. As seen in FIG. 1, the termini 82 of the tubes 76 are angled downwardly in the direction of the dental bur. As seen in FIG. 4, the termini 82 are laterally spaced on the bottom of neck 30 of handle 22. The glass fiber bundles 74 terminate at apertures 84 at the ends of tubes 76. The glass fibers are highly polished at the apertures. The glass fibers are also highly polished at their other point of termination, which is at the rear end of sleeve 66 (FIG. 6).

Referring to FIG. 6, it is seen that connector sleeve 28 includes internal threads 88 which are threadedly secured on threads 44 of adaptor nut 38. Sleeve 28 also includes an internal annular shoulder 90. An adaptor plate 92 is slidably mounted in cylindrical section 42 of adaptor nut 38. Plate 92 includes an upper lip 94 and a lower lip 96 at the rear thereof. Lips 94 and 96 abut shoulder 90, and when connector sleeve 28 is threadedly secured in place, the connector plate 92 is likewise secured in place by the shoulder 90.

Figure 8:
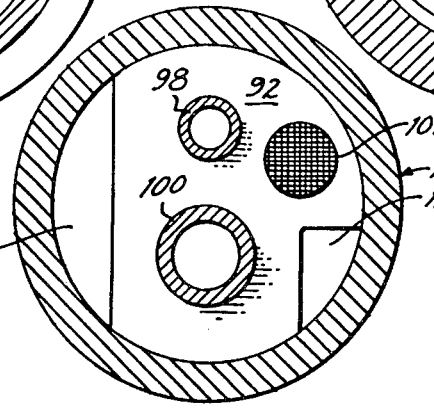
FIG. 8 is an enlarged sectional view taken along the line 8—8 of FIG. 6.

As seen in FIG. 8, adaptor plate 92 has a metal water tube 98 secured therein, a metal air tube 100 secured therein and a fiber optic bundle 102 secured therein. The metal tubes 98 and 100 are welded or soldered in place, and the fiber optic bundle 102 is adhesively secured in place. As seen in FIG. 6, a flexible tube 104 covers the fiber optic bundle, a flexible tube 106 is frictionally held on air tube 100 and a flexible tube 108 (FIG. 1) is frictionally held on water tube 98. The flexible tubes can be formed from any of the fluid carrying materials known to the art, such as rubber or polyvinyl chloride.

Referring again to FIG. 8, it is seen that there is an opening 110 formed between plate 92 and the internal wall of connector sleeve 28. Likewise, there is a second opening 112 formed between the connector plate and the connector sleeve. Openings 110 and 70 and openings 112 and 72 are respectively aligned with each other in order to create conduits for the exhausting of air from the turbine through the back of the handpiece.

Figure 5:
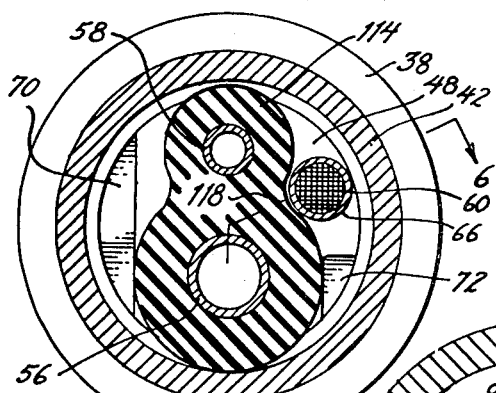
FIG. 5 is an enlarged sectional view taken along the line 5—5 of FIG. 1.

A gasket 114 is positioned between plate 48 and plate 92. Gasket 114 is formed from rubber, and water tube 58 and air tube 56 pass through the gasket. When the connector sleeve 28 is secured in place with the connector 92 therein, the water tube and air tube are received in channels within the connector. One of these channels is shown at 116 in FIG. 6, with respect to air tube 56. Metal sleeve 66 containing the fiber optic bundle 60 is cleared by a notch 118 formed on the side of the gasket (FIG. 5).

When the connector sleeve 28 is secured on handle 22, along with connector 92, sources of all of the media needed for the operation of the handpiece are automatically secured in place. Thus, air and water are supplied through flexible tubes 106 and 108 to tubes 56 and 58, respectively. The gasket 114 provides a fluid-tight connection for these tubes. The tubes 106 and 108 are also connected to suitable sources of air and water, as is common in the art.

One of the features of the device of this invention is the manner of supplying light to the fiber optic bundle 60. Thus, when the connector 92 is secured in place, the leading face of fiber optic bundle 102, which is highly polished, is automatically brought into alignment with the trailing face of the fiber optic bundle 60, which is adjacent gasket 114. As pointed out above, the sleeve 66 containing the fiber optic bundle 60 is slidably mounted within plate 48, and normally projects slightly beyond the rear edge of gasket 114. When the connector is secured in the position shown in FIG. 6, the leading edge of the bundle 102 contacts the trailing edge of the bundle 60, and slightly compresses the bundle in view of the slidable mounting of the sleeve 66 in plate 48. Thus, the resilient nature of the elastomeric sleeve 64 of bundle 60 tends to force the bundle rearwardly through the opening in plate 48. The rearward movement is stopped by the abutment of lip 68 of sleeve 66 against the plate 48. When the bundle 102 is brought in contact with sleeve 66, the sleeve 66 is pushed forwardly against the urging of the elastomeric sleeve. This assures good contact of the abutting faces of the fiber optic bundles and therefore effective light transmission through the interface of the two bundles.

The plastic tube 104 carrying the fiber optic bundle 102 is mounted at its remote end to a light source, in a manner common to all fiber optic systems. This light source is generally a lamp which is focused on the fiber optic bundle, and the bundle 102 will in turn transmit the light to the bundle 60. The light then emanates from the apertures 84 (FIG. 4) in the exposed termini 82 of the steel tubes 76. This light will then illuminate the area around the rotating dental bur 80.

Referring to FIG. 1, it is seen that water tube 58, which is rigid, is connected through flexible tubing 122 to a rigid spray tube 120 (FIG. 4). Likewise, a rigid tube 124 (FIG. 1) is tapped into air tube 56. Tube 124 is connected to a rigid spray tube 126 by flexible tubing 128. Tubes 120 and 126 are secured to a clip 130, which is in turn slidably mounted on neck portion 30 of handle 22.

Tubes 120 and 126 each contain downwardly disposed apertures 132 at the ends thereof. The tubes 120 and 126 are slidable into and out of the area of the bur 80 by sliding the clip 130 on neck portion 30. The sliding is accomplishable in view of the fact that the flexible tubes 122 and 128 can be contracted or expanded. When the spray system is in use, water will be expelled through the apertures in tube 120 and air will be expelled through the apertures in tube 126. The air will then atomize the water into a mist.

The spray system used on the handpiece of this invention is old in the art, and in itself forms no part of the invention. For a further description of the spray system, reference is made to U.S. Pat. No. 3,120,706 and 3,199,196, the disclosures of which are incorporated by reference herein. Any spray system known to the art can be used with the handpiece of this invention.

As best seen in FIG. 2, 3 and 9, turbine housing 32 is basically cylindrical, and projects perpendicularly to neck portion 30 of handle 22. Housing 32 has an end cap 134 threadedly secured on its top and an end cap 136 threadedly secured at its bottom. End cap 134 includes a central opening 138 for the reception of a chuck wrench, as will be explained hereinafter. End cap 136 also has a central opening 140, through which dental bur 80 is inserted.

A turbine cartridge 142 is inserted in turbine housing 32 by removing the end caps 134 and 136, and sliding the cartridge in place. As been seen in FIG. 9, the cartridge comprises a rotor shaft 144 having a collet 146 threadedly secured therein. A rotor having a hub 148 and spaced blades 150 is keyed to rotor shaft 144 on the outer surface thereof. Rotor shaft 144 is mounted in an upper ball bearing 152 and a lower ball bearing 154. The turbine cartridge comprises a single unit consisting of the upper and lower ball bearings, the rotor, the rotor shaft and the collet. This unit is integrally insertable and removable from the turbine housing 32.

To the extent described, the turbine cartridge is the same as that disclosed in U.S. Pat. No. 3,120,706. The insertion and removal of the turbine cartridge are discussed in further detail in said patent. As explained in said patent, the rotor shaft 144 includes an inwardly tapering wall 156 at its bottom. Likewise, the exterior wall of the collet sleeve 146 is inwardly tapering, as shown at 158 in FIG. 9. The collet includes a pair of diametrically opposed slots (one shown in phantom at 160 in FIG. 9), which slots divide the collet into a pair of jaws. The top of collet 146 is provided with a bore 162 of non-circular cross-section. In the embodiment of the invention shown, the bore has a hexagonal cross-section. As will be explained hereinafter, the rotation of the collet 146 in rotor shaft 144 causes the compression of the jaws of the collet, thereby securing the shaft of bur 80 within the collet.

As seen in FIG. 9, ball bearings 152 and 154 each comprise an inner race 164, an outer race 166 and a plurality of balls 168. The outer races 166 are contacted by the inner surfaces of the end caps 134 and 136 when the turbine cartridge is secured in place. However, each end cap is provided with an internal recess whereby the end caps will not be contacted by the inner races 164. Accordingly, the rotor shaft is freely rotatable, along with the inner races, between the end caps 134 and 136.

As seen in FIG. 2, air tube 56 is provided with a coupling 170 at its inner end. A pair of rigid tubes 172 and 174 mounted in coupling 170 and projects therefrom. As seen in FIG. 2, tubes 172 and 174 are mounted in horizontally aligned openings in turbine housing 32. As further seen in FIG. 2, the tubes 172 and 174 project angularly into the turbine housing, and in the direction of rotation of the rotor blades 150.

As seen in FIG. 3, turbine housing 32 includes a pair of openings 176 and 178. These openings are positioned above and below tube 172, and place the interior of neck 30 in fluid communication with the interior of turbine housing 32. Openings 176 and 178 are used for exhausting the air which drives the rotor.

The rotor in the handpiece of this invention is a Pelton wheel. Thus, as seen in FIG. 3, each rotor blade 150 includes a pair of aligned recesses 180. The advantage of having the recesses in the rotor blades is that a greater amount of energy is extracted from the moving air in turning the rotor when the air contacts the recessed blades, as opposed to contacting the flat blades of the prior art. As seen in FIG. 3, the recesses 178 extend axially on the rotor blades.

The details of the wrench 34 are best seen in FIG. 9. Thus, as seen therein, the wrench 34 comprises a housing 182, a tube 184 secured in a central opening in the housing and projecting vertically, a shaft 186 rotatably mounted in tube 184 and a cap 188 secured to the shaft 186. Housing 182 includes a lower cavity 190 which is basically circular in cross-section. Cavity 190 has an internal diameter which is slightly larger than the external diameter of turbine housing 32. An arcuate slot 192 is formed in cavity 190. An annular groove is formed on the wall of cavity 190, and a circular spring 194 is mounted in the groove. Spring 194 is provided with a cut 196 therethrough, in order to permit for the expansion of the spring when the wrench 34 is secured in place.

Tube 184 is secured in housing 182, and includes a pair of diametrically opposed slots 198 at the bottom thereof (see FIG. 11). A pair of downwardly projecting fingers 200 is formed by the slots 198. Shaft 186 has a hexagonal cross-section. This is the same cross-section as the cross-section of bore 162 of collet 146. Shaft 186 can have any non-circular cross-section, which cross-section, however, should be the same as the cross-section of the bore 162.

A sleeve 202 is keyed to shaft 186 and is positioned within tube 184. Tube 184 includes an inwardly projecting annular lip 204 at the top thereof. Cap 188 is also keyed to shaft 186. Thus, sleeve 202 prevents shaft 186 from being pulled upwardly through the top of tube 104 by the abutment of the sleeve against lip 204, and cap 188 prevents the shaft 186 from falling downwardly through tube 184. The rotation of cap 188 will in turn rotate shaft 186, and its associated sleeve 202, within tube 184.

Rotor shaft 144 is provided with a pair of slots 208 (FIG. 10) at the top thereof. Each slot 208 is slightly larger than a finger 198 on tube 184. As seen in FIG. 10, slots 208 are accessible through opening 138 in end cap 134. Neck 30 of handle 22 is provided with a recess 210 at its top.

The use of wrench 34 is shown in FIGS. 12 and 13. As seen in FIG. 12, housing 182 is slid downwardly over turbine housing 32, in the direction of arrow 212. Shaft 186 automatically enters bor 162 in collet 146 when this is done. The bottom of rotor shaft 144, which projects slightly through end cap 136 is then rotated until the fingers 200 are aligned with slots 208 in rotor shaft 144. When this occurs, downward pressure on housing 182 is continued, in the direction of arrows 214 of FIG. 13, until the fingers are received in the slots.

The final, secured position for the wrench 34 is shown in FIG. 13. As seen therein, the spring ring 194 has been expanded, and securely clamps the side wall of upper end cap 134. The wall of slot 192 of housing 182 is received in recess 210 of neck 30. The opening 138 in end cap 134 is sufficiently large to permit the insertion of tube 184 through the end cap.

After the wrench has been secured in place, it is ready for use in securing or removing a bur 80 from collet 146. Referring again to FIG. 13, once the shaft of bur 80 has been inserted in collet 146, cap 188 is rotated in a clockwise direction, as indicated by arrow 216. The rotation of the cap will in turn rotate shaft 186 and its associated sleeve 202. Since the shaft is received in the bore 162 of collet 146, the collet will also be rotated in a clockwise direction. The rotor 144 will be prevented from rotating by the engagement of fingers 200 in slots 208 of the rotor. Thus, the tube 184 is held rigidly in place by the engagement of the housing 182 on the turbine housing and by the abutment of the wall of slot 192 against neck 30 of the handle of the handpiece. Accordingly, the collet will rotate relative to the rotor shaft.

The rotation of the collet in a clockwise direction will move the collet vertically downward within the rotor shaft. The abutment of the tapered wall 158 of the collet against the tapered wall 156 of the rotor shaft will compress the jaws of the collet. This in turn will securely clamp the dental bur within the collet. At this point, when the turbine is rotated, the dental bur will be rotated therewith.

When it is desired to remove the dental bur, the wrench 34 is secured in place in the manner described above. However, the cap 188 is rotated in a counterclockwise direction. This raises the collet vertically within the rotor shaft, thereby permitting the jaws to expand. With the jaws thus expanded, the dental bur 80 will drop out of the collet. A new collet can then be inserted and tightened in the manner described above.

The wrench 34 of this invention possesses a number of advantages over the similar wrenches presently in use. Since the tube 184 is inserted directly through a large opening in the end cap 134, there is no problem with the attempted blind alignment of pins through small openings in the end cap and into openings in the top of a flange on the rotor. Additionally, since slots are provided directly in the top of the rotor, which slots are visible through the opening 138 in end cap 134, there is no need for the flange at the top of the rotor. This permits the use of a smaller height to the turbine housing, since no room need be provided for the rotor flange.

The air turbine is operated in the same manner as the prior art air turbines. The control for the air can be any of the conventional controls, such as a foot pedal. The air for driving the turbine enters the handpiece through tube 106, and then passes into tube 56. As seen in FIG. 2, the air is split and emanates from tubes 172 and 174 against a pair of adjacent rotor blades 150. The air is received in the arcuate recesses 178 of the rotor blades, and will drive the rotor or turbine.

As seen in FIG. 3, after the air is used to rotate the turbine, it is exhausted through openings or ports 176 and 178. It then passes rearwardly through the hollow handle 22, and is exhausted through the open end of connector sleeve 28. Referring to FIGS. 7 and 8, it is seen that the openings on the sides of plates 48 and 92 provide channels for the exhausting of the air.

The fiber optic system utilized in this invention includes glass fiber bundles. The glass fibers are preferred because they are autoclavable, and will encounter less scratching in use. However, any light transmitting fibers known to the art can be used in carrying out this invention. Thus, plastic fibers, such as polymethyl methacrylate, can also be used. These fibers can be encapsulated and sheathed in any resilient jacket, such as polyethylene, a silicone resin or polyvinyl chloride.

Having the dual light sources at apertures 84 (FIG. 4) insures continued lighting of the area of the mouth being treated, regardless of the angle at which the dentist holds the handpiece. Thus, if one of the light sources is blocked, the other will not be. There is no need for continual readjustment of the light source, as is necessary when using the externally clipped fiber optic systems presently in use. The fiber optic system of this invention is contained entirely within the handpiece, and is not disturbed during use. The rigid termini 82 of the stainless steel tube 76 are held securely in place in the position shown in FIG. 4.

The fiber optic system of this invention enjoys all of the other advantages of the prior art fiber optic system. Thus, light is transmitted from a remote source, and is easily carried around bends or curves. Thus, regardless of the manner in which the dentist will twist the handpiece, the fiber optic system will still carry light from its light source, which is at a remote point, such as on the dentist's console.

The manner of connecting the fiber optic system, as best seen in FIG. 6, is also unique. The handpiece can be used either with or without a source of light and a fiber optic system. Thus, the handpiece can be coupled to an air and water supply, without being coupled to a light source, and still carry out its intended functions. Likewise, a handpiece without the fiber optic system can be connected to the connector plate 92. The coupling of the fiber optic system to the light source is automatic when the connector is secured in place, and the resilient abutment of the glass fiber bundle 102 with the end of the glass fiber bundle 60 insures efficient light transmission and continuity.

Without further elaboration, the foregoing will so fully illustrate our invention, that others may, be applying current or future knowledge, readily adapt the same for use under various conditions of service.

What is claimed as the invention is:

1. A wrench for use on a dental handpiece having a turbine housing, a rotor shaft, and a collet threadedly secured in said rotor shaft, said wrench comprising a housing, said wrench housing being adapted to be placed over the turbine housing of said dental handpiece, a tube mounted in said wrench housing, said tube being secured to said wrench housing, said wrench housing having a cavity formed therein, means within said cavity for securing said wrench housing on said turbine housing, said securing means comprising a spring, said spring being positioned within a groove formed in the wall of said cavity, said tube having a finger which is adapted to be received in a slot in the rotor shaft of said handpiece, and a shaft rotatably mounted within said tube, said shaft being adapted to threadedly advance or retract said collet relative to said rotor shaft.

2. The wrench of claim 1 wherein said spring comprises a ring having an opening formed therein, said ring being expandable at said opening, and wherein said groove is an annular groove.

3. A wrench for use on a dental handpiece having a turbine housing, a rotor shaft and a collet threadedly secured in said rotor shaft, said wrench comprising a housing, said wrench housing being adapted to be placed over the turbine housing of said dental handpiece, a tube mounted in said wrench housing, said tube being secured to said wrench housing, said tube having a plurality of fingers formed thereon which are adapted to be received in slots in the rotor shaft of said handpiece, and a shaft rotatably mounted within said tube, said shaft being adapted to threadedly advance or retract said collet relative to said rotor shaft.

4. A wrench for use on a dental handpiece having a turbine housing, a rotor shaft and a collet threadedly secured in said rotor shaft, said wrench comprising a housing, said wrench housing being adapted to be placed over the turbine housing of said dental handpiece, a tube mounted in said wrench housing, said tube being secured to said wrench housing, said tube having a finger which is adapted to be received in a slot in the rotor shaft of said handpiece, and a shaft rotatably mounted within said tube, said shaft having a noncircular cross-section, said shaft being adapted to threadedly advance or retract said collet relative to said rotor shaft.

5. A wrench for use on a dental handpiece having a turbine housing, a rotor shaft and a collet threadedly secured in said rotor shaft, said wrench comprising a housing, said wrench housing being adapted to be placed over the tubine housing of said dental handpiece, a tube mounted in said wrench housing, said tube being secured to said wrench housing, said tube having a finger which is adapted to be received in a slot in the rotor shaft of said handpiece, and a shaft rotatably mounted within said tube, a cap secured to said shaft, said cap being adapted to rotate said shaft relative to said tube, said shaft being adapted to threadedly advance or retract said collet relative to said rotor shaft.

* * * * *